(12) United States Patent
Bagaoisan et al.

(10) Patent No.: US 12,343,504 B2
(45) Date of Patent: Jul. 1, 2025

(54) DEVICES, SYSTEMS, AND METHODS FOR THE EMBOLIZATION OF BODY LUMENS

(71) Applicant: BlackSwan Vascular, Inc., Hayward, CA (US)

(72) Inventors: Celso J. Bagaoisan, Union City, CA (US); Suresh S. Pai, Los Altos, CA (US); Scott Robert Sershen, Castro Valley, CA (US)

(73) Assignee: BLACKSWAN VASCULAR, INC., Hayward, CA (US)

( * ) Notice: Subject to any disclaimer, the term of this patent is extended or adjusted under 35 U.S.C. 154(b) by 0 days.

(21) Appl. No.: 16/433,758

(22) Filed: Jun. 6, 2019

(65) Prior Publication Data

US 2019/0350592 A1 Nov. 21, 2019

Related U.S. Application Data

(63) Continuation of application No. PCT/US2017/065472, filed on Dec. 8, 2017.
(Continued)

(51) Int. Cl.
*A61M 5/19* (2006.01)
*A61M 5/14* (2006.01)
(Continued)

(52) U.S. Cl.
CPC ............ *A61M 5/19* (2013.01); *A61M 5/1408* (2013.01); *A61M 5/1452* (2013.01);
(Continued)

(58) Field of Classification Search
CPC ........ A61B 17/12186; A61B 17/12109; A61B 17/12113; A61B 2017/00495;
(Continued)

(56) References Cited

U.S. PATENT DOCUMENTS 5,851,508 A 12/1998 Greff et al.
6,062,722 A 5/2000 Lake
(Continued)

FOREIGN PATENT DOCUMENTS

WO 9608227 A1 3/1996
WO 2016149457 A1 9/2016

OTHER PUBLICATIONS

"adjacent.", 2011, Houghton Mifflin Harcourt Publishing Company, American Heritage® Dictionary of the English Language, Fifth Edition. (Year: 2011).*
(Continued)

*Primary Examiner* — Kami A Bosworth
*Assistant Examiner* — Avery Smale
(74) *Attorney, Agent, or Firm* — William A. English; Vista IP Law Group LLP

(57) ABSTRACT

Systems and methods for embolizing body lumens are provided that include a mixing component provided in a flow path between two chambers, e.g., syringes, such that one or more actuators may direct embolic material back and forth between the two chambers through the mixing component to mix the embolic material. Once mixed, the embolic material may be delivered from one of the chambers through a catheter into a patient's body to embolize a target location.

23 Claims, 7 Drawing Sheets

Related U.S. Application Data

(60) Provisional application No. 62/431,424, filed on Dec. 8, 2016.

(51) Int. Cl.
 *A61M 5/145* (2006.01)
 *A61M 5/28* (2006.01)
 *A61M 39/22* (2006.01)
 *B01F 101/00* (2022.01)

(52) U.S. Cl.
 CPC ....... *A61M 5/284* (2013.01); *A61M 2039/229* (2013.01); *B01F 2101/2202* (2022.01)

(58) Field of Classification Search
 CPC ........ A61B 2017/1205; A61M 5/1408; A61M 5/1452; A61M 2039/229; A61M 5/284; A61M 5/19; A61M 2005/3114; A61M 2005/3115; A61M 2039/0027; A61M 39/223; A61M 5/1407; A61M 5/1409; A61M 5/16827; A61M 5/2066; A61M 5/2448; A61M 5/31596; B01F 5/0615; B01F 13/0023; B01F 15/0237; B01F 2215/0034; B01F 5/0685; B01F 25/43141; B01F 33/50112; B01F 35/7174; B01F 25/4512; B01F 2101/2202
 See application file for complete search history.

(56) References Cited

U.S. PATENT DOCUMENTS

| | | | |
|---|---|---|---|
| 9,107,668 B2 | 8/2015 | Melsheimer et al. | |
| 2004/0054320 A1* | 3/2004 | Kissinger | A61B 5/150854 604/93.01 |
| 2005/0209555 A1* | 9/2005 | Middleton | A61J 1/2096 604/82 |
| 2009/0043277 A1* | 2/2009 | Sturtevant | A61B 17/1219 604/502 |
| 2009/0247985 A1* | 10/2009 | Melsheimer | A61J 1/2096 604/506 |
| 2010/0091606 A1* | 4/2010 | Kwan | B01F 15/0258 366/139 |
| 2013/0253430 A1* | 9/2013 | Kouyoumjian | A61M 5/16827 604/151 |
| 2015/0290078 A1 | 10/2015 | Li et al. | |
| 2016/0157910 A1 | 6/2016 | Phan et al. | |
| 2016/0166761 A1* | 6/2016 | Piehl | A61B 17/3498 604/207 |

OTHER PUBLICATIONS

"outlet.", 2011, Houghton Mifflin Harcourt Publishing Company, American Heritage® Dictionary of the English Language, Fifth Edition. (Year: 2011).*

Sang Won Choi, Korean Intellectual Property Office, International Search Report and Written Opinion from corresponding International Application No. PCT/US2017/065472, Apr. 25, 2018, 25 pages.

B. Krasenbrink, European Patent Office, Supplementary European Search Report and Response for corresponding European Patent Application No. EP 17878388, Jul. 9, 2020, 23 pages.

\* cited by examiner

DEVICES, SYSTEMS, AND METHODS FOR THE EMBOLIZATION OF BODY LUMENS

RELATED APPLICATION DATA

The present application is a continuation of co-pending international application No. PCT/US2017/065472, filed Dec. 8, 2017, which claims benefit of U.S. provisional application Ser. No. 62/431,424, filed Dec. 8, 2016, the entire disclosures of which are expressly incorporated by reference.

FIELD OF THE INVENTION

The present invention relates generally to system and methods for embolizing body lumens, and, more particularly, to systems and methods for mixing liquid embolic material immediately before delivery into a patient's body.

BACKGROUND

The embolization, or blocking off, of body lumens is a well-established minimally invasive surgical technique for treating malformations, diseases, or damage to a variety of body lumens. The technique is frequently used for embolization of aberrant or undesired blood flow to arteriovenous malformations, uterine fibroids, tumors, varicoceles and aneurysms (e.g., in the neurovascular and peripheral vascular space), as well as to treat bleeding in the gastrointestinal tract or due to trauma. At a high level, these procedures all involve a relatively common approach wherein a catheter is inserted into the vasculature and advanced either into or proximal to a target location and an embolic agent is delivered through the catheter and into the target location. The embolic agent then blocks blood from flowing into the target location. This may be done (for example) to stabilize a weakened artery with thin walls (in the case of an aneurysm), to occlude a mass of abnormal connections between the arterial and vascular halves of the circulatory system (in the case of an arteriovenous malformation), to prevent blood flow to a tumor as part of a cancer therapy, or to mitigate aggressive bleeding from an ulcer or other bleeding injury to the gastrointestinal tract.

It may also be performed after completion of an endovascular aneurysm repair (EVAR) procedure. In an EVAR procedure, a fabric covered stent or stent graft is placed within the weakened section of the aorta to provide reinforcement and to hydraulically isolate this segment to mitigate the potential for aortic rupture. Some 15-25% of such treated patients undergo a complication known as an endoleak wherein some amount of blood flow still remains in the aneurysm cavity. The most common type of endoleak presentation (typically called a type II endoleak) occurs when blood continues to flow into the aneurysmal sac from side branch arteries of the treated aorta.

A wide variety of embolic agents have been used for this purpose, including stainless steel and platinum coils, polyvinyl alcohol or gelatin-impregnated acrylic spheres, cyanoacrylates, ethylene vinyl alcohols, as well as sclerosing agents such as alcohols. Each of these broad categories of embolic agents are suited for particular applications based on their individual strengths and weaknesses. For example, a stainless steel embolic coil system allows the operator to proceed at a very measured pace as the coils are not dropped out or released from the distal end of the catheter until the physician initiates that action. This feature enables a physician operator to position or re-position the coil(s) until they are in the optimal arrangement based on the physician's understanding of the particular clinical presentation under treatment.

However, a drawback of coil systems is that they do not conform to the asymmetrical, irregular and/or sometimes highly tortuous anatomical profiles of many target embolic sites, providing inadequate filling and thereby leaving an undesired and incomplete embolization outcome. Furthermore, such coil delivery systems can have higher than desired delivery profiles and stiffness and this limitation can prohibit usage in target anatomies where the embolic target is significantly more distal than the location at which the coil delivery system can be safely be positioned.

On the other hand, a liquid embolic has the benefit of completely filling the space into which it is introduced and potentially filling a greater volume of space (such as the treatment of a large arteriovenous malformation in the peripheral vascular system). A liquid embolic can typically be injected into the body and can more easily reach anatomical targets that are significantly distal to the tip of the delivery system. These benefits do not come without a cost, as controlling where the liquid embolic flows and exactly how it fills the target space is less strictly controlled by the operator when compared to the solid coil systems. Once a liquid embolic is injected through a catheter, the physician operator has much less control over where the embolic ends up than with the coil systems. In both cases, training, skill, and the familiarity of the physician user with the chosen embolic system will greatly mitigate the downsides (i.e., the morbidity and mortality) associated with the clinical use of any of these systems.

One feature of many of the commercially available embolic systems is the inclusion of radiopaque materials to allow the user to determine the extent of the embolization in real time, e.g., using a fluoroscope. In the case of stainless steel or platinum coils, the radiopaque characteristic is an inherent quality of the embolic materials themselves. If the embolic material is not radiopaque, an additional component is often added to the system to provide this feature. One of the most commonly used liquid embolic systems is the Onyx Liquid Embolic System (Medtronic), a suspension of micronized tantalum in a solution of dimethyl sulfoxide (DMSO) and ethylene vinyl alcohol (EVOH). EVOH is soluble in DMSO, but not in aqueous media, and therefore rapidly precipitates to form a solid when the suspension is introduced into an aqueous environment due to the diffusion of DMSO into the aqueous medium.

The inclusion of tantalum particles provides radiopacity adequate to provide feedback to the physician operator to guide the deposition of the liquid embolic under fluoroscopic guidance. The tantalum particles are large enough that they are captured within the precipitating EVOH and do not diffuse away from the embolic site over time, providing a clear, high-contrast signal to the operator during fluoroscopic interrogation of the treatment site. However, at a density of 16.69 grams per cubic centimeter at room temperature, tantalum is a very heavy metal and the tantalum particulate can sink to the bottom of an EVOH/DMSO solution in an order of minutes. Thus, one challenge of using Onyx is achieving and maintaining a relatively homogenous suspension of tantalum in the EVOH/DMSO solution.

The instructions for use state that a single serum vial containing the EVOH/DMSO/tantalum suspension should be agitated on a vortex mixer for twenty (20) minutes prior to use, and if the mixed suspension is not used within five (5) minutes post mixing, the agitation of the vial must be repeated. This requirement places a significant amount of strain on the physician and operating room staff, as the preparation of the Onyx liquid embolic has to be timed to align with the needs of the procedure and a twenty (20) minute lead time is a considerable obstacle to plan around. These requirements make Onyx challenging to use in complicated cases where there may be a protracted procedure time wherein the tantalum may settle intra-procedurally (i.e., a treatment that extends beyond the specified five minute window), as well as in emergent cases (e.g., bleeds due to trauma) where more rapid action or vascular intervention is required.

Thus, there exists a need for embolic devices, systems, and methods that retain the beneficial aspects of existing liquid embolic systems and mitigate or eliminate the time-consuming steps needed to prepare these systems for use.

SUMMARY

The present invention is directed to systems and methods for embolizing body lumens, and, more particularly, to systems and methods for mixing liquid embolic material immediately before delivery into a patient's body.

Described herein are devices, systems, and methods to embolize body lumens. The devices generally comprise an elongate member that further comprises static mixing elements along with connecting elements on the proximal, and optionally, the distal ends. Additional components such as valves, flow directing components, shells, housings, handles, actuators, and the like may be included in systems and methods.

Static mixing is a technique wherein the materials to be mixed are directed through a flow path that contains elements that act to mix the materials without the input of external power. The elements may be vanes or other features that protrude into the flow path to create turbulence that in turn mixes the materials of interest. This system is known as a plate-type system, and incorporates a method for delivering two or more streams of fluids or materials into the static mixer. As the streams move through the mixer, the non-moving elements continuously blend the materials. Complete mixing depends on many variables including the fluids' properties, tube inner diameter, number of elements and their design. A thorough discussion of plate-type static mixing systems that may be included in the systems and methods herein is provided in U.S. Pat. Nos. 5,839,828, 7,281,844, 8,147,124, 9,067,183, and 9,221,022, the entire disclosures of which are expressly incorporated by reference herein.

An alternative type of system houses a series of helical or pseudo-helical elements arranged in a series of alternating left and right hand 180° twists within a hollow tube or elongate member. The leading edge of an element, which is on a diameter, is offset, e.g., at 90°, to the trailing edge of the adjacent upstream element. This arrangement is an example of the mechanisms of mixing that may be included in the systems and methods described herein. One, flow division, dominates for mixtures with Reynolds numbers that are generally less than 2000. The second, radial mixing, becomes a contributing factor at higher Reynolds numbers (generally in excess of 2000).

In flow division, the leading edge of the first element splits the fluids entering the mixer into two streams, which are then rotated through 180°. The second element splits the flow again, this time into four streams, followed by a further rotation, in the opposite direction, through 180°. The third element repeats the process by splitting into eight streams, and so on. As the number of streams or layers increases, the layer thickness decreases. The quality and thoroughness of the resultant mixture is a function of only the mixer diameter and the number of mixing elements, and is independent of flow rate and mixture viscosity. This is beneficial in that a high pressure and/or high flow rate are not required to achieve consistent mixing. In practice, mixing via flow division allows for homogeneity of the resultant mixture at low delivery speeds. For example, a liquid embolic can be delivered at a methodical rate and be fully mixed throughout the span of the delivery.

Radial mixing is often associated with low viscosity mixtures that experience turbulent flow. Under these conditions, the element shape is able to impart a rotational spin to the fluids, which changes direction with each succeeding element. Fluids are constantly moved from the pipe center to the pipe wall and back again, with the interface between elements creating a particularly active mixing zone. This mechanism of mixing dominates in turbulent flow, and is able to rapidly eliminate radial gradients or differences in, for example, pH, composition, color, temperature, and velocity of the mixed substances. Of note is the fact that radial mixing is generally more efficient than flow division, with radial mixing requiring anywhere from threefold to sixteen-fold fewer mixing elements than flow division. Another common type of static mixing element is a square mixing element comprising alternating left- and right-hand elements with intermittent flow inverters that channel fluids from the walls of the mixer to the center of the mixer and from center to walls.

The amount of mixing for a given mixture may be increased by passing the mixing components through the static mixer multiple times. For example, a chamber may be joined to the proximal end of the static mixer and a second chamber may be joined to the distal end of the static mixer such that the mixing components may be repetitively passed from the proximal chamber to the distal chamber to achieve greater mixing than would be achieved with a single pass.

In accordance with one embodiment of the systems and methods herein, a mixing component is provided that includes an elongate member that has distal and proximal ends. The outer surface of the elongate member may be elliptical or rectilinear in cross section, and the diameter or outer dimensions of the elongate member may be constant or may vary along the length of the elongate member. For example, the elongate member may be circular in cross section with an outer diameter of 0.250" at the proximal end and 0.125" at the distal end, wherein the transition from the proximal outer diameter to distal outer diameter is a linear reduction.

Alternatively, the profile of the outer diameter of the elongate member may include multiple linear reductions or increases, multiple inward or outward curving segments, multiple step changes in diameter, combinations thereof, or any shape over the length of the elongate member. Likewise, the geometry of the cross-section of the elongate member may be fixed or variable over the length of the elongate member. For example, an elongate member may include a segment that is square in cross-section, a segment that is elliptical in cross-section, and a segment that is octagonal in cross-section, with the sections connected by sweeps, surfaces, extrusions, and like as previously described. It should be obvious to one of skill in the art that any combination of size, profile, and cross-sectional geometry is contemplated.

Furthermore, other characteristics of the elongate member may be fixed or variable over the length and/or the radius and azimuth of the cross section of the elongate member including, but not limited to, color, stiffness, density, strength, ductility, elasticity, hydrophobicity, hydrophilicity, compressive modulus, opacity, transparency, radiopacity, chemical compatibility, melting temperature, glass transition temperature, thermal conductivity, dielectric constant, resistance, permittivity, combinations thereof, and the like. The elongate member may further include at least one lumen. The at least one lumen may be elliptical or rectilinear in cross-section, and may have any cross-sectional dimension that may be contained within the outer measure of the elongate member.

For example, an elongate member with a fixed, circular cross-section and a diameter of 0.130" may have a single lumen of a circular cross section that is less than 0.130" at its greater diameter. The geometry and cross-sectional size of the lumen may be sized to accommodate the placement of at least one static mixing element within the lumen. For example, the lumen may be circular in cross-section and have a diameter of less than 0.050", 0.050" to 0.075", 0.075" to 0.100", 0.100" to 0.125", 0.125" to 0.150", 0.150" to 0.175", 0.175" to 0.200", 0.200" to 0.225", 0.225" to 0.250", or greater than 0.250". In an exemplary embodiment, the lumen may be circular in cross-section and have a diameter of 0.075" to 0.100". While these examples have used circular elongate members with circular lumens for demonstration, it should be clear to one of skill in the art that other geometries are contemplated.

As another example, a square elongate member with a square lumen that is sized to accept squared-off helical static mixing elements may be provided. The elongate member may be fabricated from materials known to the art including, but not limited to, aliphatic polyamides, fluorinated ethylene propylene, nylon, perfluoroalkoxy (e.g., Teflon®), polyether block amide (Pebax®), polyetheretherketone (PEEK), polyethylene, polytetrafluoroethylene (PTFE), polypropylene, polyurethane, polyvinylchloride, polysulfone, stainless steel, nickel, titanium, aluminum, brass, copper, platinum, polycarbonate, acrylic, polyoxymethylene (Delrin®), combinations and/or alloys thereof, and the like. In an exemplary embodiment, the elongate member may be fabricated out of a material that is compatible with DMSO, such as polypropylene, nylon, polyoxymethylene and the like.

An elongate member that includes at least one lumen may further include internal features, such as protrusions, flanges and the like that may extend into the lumen. These features may be an inherent part of the elongate member (e.g., as formed by injection molding) or may be components of differing materials that are joined to the elongate member using means known to the art including, but not limited to bonding, welding, ultrasonic welding, over-molding, threading/tapping, crimping, press or interference fits, combinations thereof, and the like.

In the case of disparate internal features joined to the elongate member, the internal features may be fabricated from materials known to the art including, but not limited to, aliphatic polyamides, fluorinated ethylene propylene, nylon, perfluoroalkoxy (e.g., Teflon®), polyether block amide (Pebax®), polyetheretherketone (PEEK), polyethylene, polytetrafluoroethylene (PTFE), polypropylene, polyurethane, polyvinylchloride, polysulfone, stainless steel, nickel, titanium, aluminum, brass, copper, platinum, polycarbonate, acrylic, polyoxymethylene (Delrin®), combinations and/or alloys thereof, and the like. In an exemplary embodiment, the elongate member may be fabricated out of a material that is compatible with DMSO, such as polypropylene, nylon, polyoxymethylene and the like. The internal features may be designed to promote turbulent mixing as described in in U.S. Pat. Nos. 5,839,828, 7,281,844, 8,147,124, 9,067,183, and 9,221,022, the entire disclosures of which are expressly incorporated by reference herein, or they may function as a stop to minimize or prevent longitudinal movement of a helical static mixing element or elements.

The elongate member may further include connecting elements on the proximal and/or, optionally, distal ends. The connecting elements may include a lumen that is in fluid communication with at least one of the lumens of the elongate member, and may be fabricated from materials known to the art including, but not limited to, aliphatic polyamides, fluorinated ethylene propylene, nylon, perfluoroalkoxy (e.g., Teflon®), polyether block amide (Pebax®), polyetheretherketone (PEEK), polyethylene, polytetrafluoroethylene (PTFE), polypropylene, polyurethane, polyvinylchloride, polysulfone, stainless steel, nickel, titanium, aluminum, brass, copper, platinum, polycarbonate, acrylic, polyoxymethylene (Delrin®), combinations and/or alloys thereof, and the like. In an exemplary embodiment, the elongate member may be fabricated out of a material that is compatible with DMSO, such as polypropylene, nylon, polyoxymethylene, and the like.

The connecting elements may take standard forms including, but not limited to, Luer-Lok® fittings (male and/or female), slip Luer fittings (male and/or female), quick-disconnect fittings (male and/or female), threaded/tapped fittings, single or multiple barbs, combinations thereof, and the like. The connecting elements may be formed as contiguous extrusions of the elongate member (e.g., via injection molding), or may be formed separately and joined to the elongate member using methods known to the art including, but not limited to, bonding, welding, ultrasonic welding, over-molding, threading/tapping, crimping, press or interference fits, combinations thereof, and the like.

For example, the systems and methods herein may include a mixing component including an elongate member with a circular cross-section of 0.188" outer diameter with a concentrically-aligned circular lumen of 0.099" in diameter, a female Luer fitting joined to the proximal end, a male Luer fitting joined to the distal end, and a twenty four (24) element helical static mixer with an outer diameter of 0.093" disposed within the lumen. The elongate member may be of a length such that the entirety of the helical static mixer is contained in the portion of the elongate member between the female and male Luer fittings. The elongate member may further include internal flanges that restrict longitudinal motion of the helical static mixers. In an exemplary embodiment, the elongate member may be fabricated of nylon or polypropylene, and the helical static mixers may be fabricated of nylon, polypropylene, or polyoxymethylene. While this example identifies a twenty four (24) element static mixer, the static mixer may include one or more elements, e.g., between 1 to 4, 4 to 8, 8 to 12, 12 to 16, 16 to 20, 20 to 24, 24 to 28, 28 to 32 or more, and the static mixer may have a length corresponding to the number of sequential elements therein. In another example, the distal male Luer fitting of the prior example may be replaced by a female Luer fitting.

In an exemplary embodiment, the system may include a capped syringe containing pure DMSO, a capped syringe containing a mixture of EVOH, DMSO, and micronized tantalum (the "suspension" syringe), and a mixing component. The ratio of EVOH to DMSO may be varied to produce a solution with a range of viscosities; in exemplary embodiments, the solutions may have a variety of viscosities, for example, less than 7 centistokes (cSt), or between about 7 to 9 cSt, 9 to 11 cSt, 11 to 13 cSt, 13 to 15 cSt, 15 to 17 cSt, 17 to 19 cSt, 19 to 21 cSt, 21 to 23 cSt, 23 to 25 cSt, 25 to 27 cSt, 27 to 29 cSt, 29 to 31 cSt, 31 to 33 cSt, 33 to 35 cSt, or greater than 35 cSt. The syringes and caps may be fabricated of materials that are compatible with DMSO. The EVOH may be any variant, for example, having an ethylene content of about 48% (mol %). The tantalum may be micronized with a range of particle sizes with an exemplary maximum particle size of not more than five (5) micrometers.

The mixing component may include an elongate member with a single lumen housing static mixing elements, a female Luer fitting on the proximal end, and a male Luer fitting on the distal end. Each of the components may be supplied sterile in appropriate packaging.

In an exemplary embodiment, a method is provided for using this system to embolize an arteriovenous malformation by positioning a DMSO-compatible catheter in the patient such that the distal end of the catheter is in a position to deliver the liquid embolic. The catheter is prepared for the delivery of the liquid embolic by removing the DMSO syringe from the packaging, removing the cap from the syringe, and flushing the DMSO-compatible catheter with DMSO to eliminate any blood, saline, or other fluid from the catheter. The suspension syringe is removed from the packaging and optionally manually agitated to achieve preliminary mixing of the tantalum within the EVOH/DMSO solution. The mixing component is removed from the packaging and placed in the sterile field using sterile technique. The cap is removed from the suspension syringe and the suspension syringe is attached to the proximal end of the mixing component. The suspension syringe is held vertically such that the distal end of the mixing component is facing upwards and the suspension syringe plunger is depressed until the void volume of the mixing component is filled with the preliminarily mixed DMSO/EVOH/tantalum suspension.

The distal end of the mixing component is connected to the hub of the DMSO-compatible catheter, and the suspension syringe plunger is depressed to deliver the fully homogenized DMSO/EVOH/tantalum suspension to the patient. The passage of the DMSO/EVOH/tantalum suspension through the mixing component is the method by which the suspension is fully homogenized. This mechanism of mixing does not require an external power or energy source and ready for use immediately due to the "on-call" nature of static mixing. While this example uses an EVOH/DMSO/tantalum suspension or mixture as an example, it should be clear to one of skill in the art that this method is applicable to other embolic agents such as non-drug and drug loaded polymeric microspheres. Such microspheres include, but are not limited to, spherical or non-spherical polyvinyl alcohol beads, tris-acryl gelatin microspheres, and the like.

In accordance with another embodiment, a system is provided that includes a capped syringe containing pure DMSO, an empty syringe, a capped syringe containing a mixture of EVOH, DMSO, and tantalum (the "suspension" syringe), and a mixing component. The ratio of EVOH to DMSO may be varied to produce a solution with a range of viscosities; it is preferable to have solutions including a variety of viscosities, for example, less than 7 centistokes (cSt), 7 or between about to 9 cSt, 9 to 11 cSt, 11 to 13 cSt, 13 to 15 cSt, 15 to 17 cSt, 17 to 19 cSt, 19 to 21 cSt, 21 to 23 cSt, 23 to 25 cSt, 25 to 27 cSt, 27 to 29 cSt, 29 to 31 cSt, 31 to 33 cSt, 33 to 35 cSt, or greater than 35 cSt. The syringes and caps may be fabricated of materials that are compatible with DMSO. The EVOH may be any variant, for example, having an ethylene content of about 48% (mol %). The tantalum may be micronized with a range of particle sizes with an exemplary maximum particle size of not more than five (5) micrometers. The mixing component includes an elongate member with a single lumen housing static mixing elements, a female Luer fitting on the proximal end, and a female Luer fitting on the distal end. Each of the components would be supplied sterile in appropriate packaging.

In accordance with another embodiment, a method is provided for using this system to embolize an arteriovenous malformation by positioning a DMSO-compatible catheter in the patient such that the distal end of the catheter is in a position to deliver the liquid embolic. The catheter is prepared for the delivery of the liquid embolic by removing the DMSO syringe from the packaging, removing the cap from the syringe, and flushing the DMSO-compatible catheter with DMSO to eliminate any blood, saline, or other fluid from the catheter. The suspension syringe is removed from the packaging and optionally manually agitated to achieve preliminary mixing of the tantalum within the EVOH/DMSO solution. The mixing component and empty syringe are removed from the packaging and placed in the sterile field using sterile technique. The cap is removed from the suspension syringe and the suspension syringe is attached to the proximal end of the mixing component. The suspension syringe is held vertically such that the distal end of the mixing component is facing upwards and the suspension syringe plunger is depressed until the void volume of the mixing component is filled with the preliminarily mixed DMSO/EVOH/tantalum suspension.

The empty syringe is connected to the distal end of the mixing component. The suspension syringe plunger is fully depressed to pass the DMSO/EVOH/tantalum suspension from the suspension syringe, through the mixing component, and to the empty, or receiving, syringe. This is referred to as a single mixing pass. A second mixing pass is performed by fully depressing the receiving syringe plunger to transfer the DMSO/EVOH/tantalum suspension from the receiving syringe, through the mixing component, and to the suspension syringe. The physician operator may optionally perform any additional number of mixing passes to fully homogenize the DMSO/EVOH/tantalum suspension. If an odd number of passes is completed, the receiving syringe (containing the DMSO/EVOH/tantalum suspension) is disconnected from the mixing component, entrained air is evacuated from the syringe, the syringe is connected to the hub of the DMSO-compatible catheter, and the syringe plunger is depressed to deliver the fully homogenized DMSO/EVOH/tantalum suspension to the patient. If an even number of passes is completed, the suspension syringe (containing the DMSO/EVOH/tantalum suspension) is disconnected from the mixing component, entrained air is evacuated from the syringe, the syringe is connected to the hub of the DMSO-compatible catheter, and the syringe plunger is depressed to deliver the fully homogenized DMSO/EVOH/tantalum suspension to the patient.

Optionally, either of the two systems previously described may further include an air-bleed filter to remove gas from the homogenized DMSO/EVOH/tantalum suspension prior to entering the DMSO-compatible syringe. While this example uses an EVOH/DMSO/tantalum suspension or mixture as an example, it should be clear to one of skill in the art that this method is applicable to other embolic agents such as polymeric microspheres including, but not limited to spherical or non-spherical polyvinyl alcohol beads, tris-acryl gelatin microspheres, and the like.

In accordance with yet another embodiment, a system is provided that includes a capped syringe containing pure DMSO, an empty syringe, a capped syringe containing a mixture of EVOH, DMSO, and tantalum (the "suspension" syringe), a three-way stopcock, and a mixing component. The syringes, caps, and three-way stopcock may be fabricated of materials that are compatible with DMSO. The ratio of EVOH to DMSO may be varied to produce a solution including a variety of viscosities, for example, less than 7 centistokes (cSt), or between about 7 to 9 cSt, 9 to 11 cSt, 11 to 13 cSt, 13 to 15 cSt, 15 to 17 cSt, 17 to 19 cSt, 19 to 21 cSt, 21 to 23 cSt, 23 to 25 cSt, 25 to 27 cSt, 27 to 29 cSt, 29 to 31 cSt, 31 to 33 cSt, 33 to 35 cSt, or greater than 35 cSt. The EVOH may be any variant, for example, an ethylene content of about 48% (mol %). The tantalum may be micronized with a range of particle sizes with an exemplary maximum particle size of not more than five (5) micrometers. The mixing component may include an elongate member with a single lumen housing static mixing elements, a female Luer fitting on the proximal end, and a male Luer fitting on the distal end. Each of the components may be supplied sterile in appropriate packaging.

In an exemplary embodiment, a method is provided for using this system to embolize an arteriovenous malformation by positioning a DMSO-compatible catheter in the patient such that the distal end of the catheter is in a position to deliver the liquid embolic. The catheter is prepared for the delivery of the liquid embolic by removing the DMSO syringe from the packaging, removing the cap from the syringe, and flushing the DMSO-compatible catheter with DMSO to eliminate any blood, saline, or other fluid from the catheter. The suspension syringe is removed from the packaging and optionally manually agitated to achieve preliminary mixing of the tantalum within the EVOH/DMSO solution. The mixing component, three-way stopcock, and empty syringe are removed from the packaging and placed in the sterile field using sterile technique. One arm of the three way stopcock is connected to the distal end of the mixing component. The cap is removed from the suspension syringe and the suspension syringe is attached to the proximal end of the mixing component. The suspension syringe is held vertically such that the stopcock is facing upwards and the suspension syringe plunger is depressed until the void volume of the mixing component and stopcock is filled with the preliminarily mixed DMSO/EVOH/tantalum suspension. The empty syringe is connected to a second arm of the three-way stopcock and the stopcock is adjusted to permit flow between the suspension syringe and the empty, or receiving, syringe. The third arm of the stopcock is connected to the hub of the DMSO-compatible catheter.

The suspension syringe plunger is fully depressed to pass the DMSO/EVOH/tantalum suspension from the suspension syringe, through the mixing component and stopcock, and to the receiving syringe. This is referred to as a single mixing pass. A second mixing pass is performed by fully depressing the receiving syringe plunger to transfer the DMSO/EVOH/tantalum suspension from the receiving syringe, through the stopcock and mixing component, and to the suspension syringe. The physician operator may optionally perform any additional number of mixing passes to fully homogenize the DMSO/EVOH/tantalum suspension. If an odd number of passes is completed, the stopcock is adjusted to permit flow from the receiving syringe (containing the DMSO/EVOH/tantalum suspension) to the hub of the DMSO-compatible catheter, and the syringe plunger is depressed to deliver the fully homogenized DMSO/EVOH/tantalum suspension to the patient. If an even number of passes is completed, the stopcock is adjusted to permit flow from the suspension syringe (containing the DMSO/EVOH/tantalum suspension) to the hub of the DMSO-compatible catheter, and the syringe plunger is depressed to deliver the fully homogenized DMSO/EVOH/tantalum suspension to the patient.

At any time during the procedure, e.g., if the procedure takes an extended amount of time and/or the physician operator wishes to further mix the DMSO/EVOH/tantalum suspension, the physician operator may adjust the stopcock to permit flow between the suspension and receiving syringes, perform as many passes of the remaining DMSO/EVOH/tantalum suspension as desired, then adjust the stopcock an additional time to permit flow between either the receiving or suspension syringe and the hub of the DMSO-compatible catheter. While this exemplary system and method of use places the mixing component between the suspension syringe and the three-way stopcock, the mixing component may alternatively be placed between the receiving syringe and the three-way stopcock.

In another embodiment, the system may include two mixing components where a mixing component is placed between, respectively, the suspension syringe and the stopcock, and the receiving syringe and the stopcock. In this case, the two mixing components may be identical or different in any of the characteristics discussed elsewhere herein for the mixing component elongate member. While the provided examples use a three-way stopcock as a mechanism to control the direction of flow, other mechanisms for directing flow may be provided including valves, two-way stopcocks, manifolds, and the like.

Furthermore, any of the systems herein may further include a housing that encloses various components and allows intuitive control of the transition between mixing and delivering the DMSO/EVOH/tantalum suspension.

While this example uses an EVOH/DMSO/tantalum suspension or mixture as an example, it should be clear to one of skill in the art that the systems and methods herein are applicable to other embolic agents such as polymeric microspheres including, but not limited to spherical or non-spherical polyvinyl alcohol beads, tris-acryl gelatin microspheres, and the like.

In accordance with still another embodiment, a system is provided that includes a capped syringe containing pure DMSO, an empty syringe (the "receiving" syringe), a syringe containing a mixture of EVOH, DMSO, and micronized tantalum (the "suspension" syringe), a two-way manifold, a housing, a spring, and a mixing component. The system may further include at least one extension line with at least one lumen to enable fluid communication between the various components. The syringes, caps, extension lines, and two-way manifold may be fabricated of materials that are compatible with DMSO. The ratio of EVOH to DMSO may include a variety of viscosities, for example, less than 7 centistokes (cSt), or between about 7 to 9 cSt, 9 to 11 cSt, 11 to 13 cSt, 13 to 15 cSt. 15 to 17 cSt, 17 to 19 cSt, 19 to 21 cSt, 21 to 23 cSt, 23 to 25 cSt, 25 to 27 cSt, 27 to 29 cSt, 29 to 31 cSt, 31 to 33 cSt, 33 to 35 cSt, or greater than 35 cSt. The EVOH may be any variant, for example, including an ethylene content of about 48% (mol %). The tantalum may be micronized with a range of particle sizes with an exemplary maximum particle size of not more than five (5) micrometers. The spring and handle may be fabricated from materials known to the art including, but not limited to, aliphatic polyamides, fluorinated ethylene propylene, nylon, perfluoroalkoxy (e.g., Teflon®), polyether block amide (Pebax®), polyetheretherketone (PEEK), polyethylene, polytetrafluoroethylene (PTFE), polypropylene, polyurethane, polyvinylchloride, polysulfone, stainless steel, nickel, titanium, aluminum, brass, copper, polycarbonate, acrylic, polyoxymethylene (Delrin®), combinations and/or alloys thereof, and the like.

The housing may be sized and shaped to accept and enclose an arrangement of the spring, the empty syringe or other receiving container, the mixing component, and the two-way manifold. The housing may further include one or more flanges, recesses, spaces, extrusions, and the like on the interior or exterior surfaces to maintain and/or allow the relative motion of the other components of the system. For example, a proximal portion of the housing may include a cavity of appropriate length and diameter to accept the spring. A portion of the housing distal to the distal end of the spring may include a pair of flanges that grip and secure the empty receiving syringe such that the syringe barrel does not move relative to the housing.

The spring may be of a length that, when fully relaxed or under no strain (i.e., not experiencing a tensile or compressive load), the proximal end of the spring is in contact with a proximal inner face of the housing and the distal end of the spring is in contact with the proximal face of the syringe plunger of the empty syringe. The distal end of the syringe, or syringe tip, may be connected either directly or via an extension line to the proximal end of the mixing component.

The distal end of the mixing component may be connected either directly or via an extension line to a port on the two-way manifold. In this example, the two-way manifold includes three ports and a mechanism to ensure that only two of the ports are in fluid communication at a given time. For illustration, the three ports will be denoted "A", "B", and "C". The manifold further restricts the permutations of flow paths by only allowing flow or fluid communication between ports A and B, or alternatively between ports B and C. A fluid path that provides communication between ports A and C is not possible due to the design of the manifold. One exemplary mechanism for achieving this design is for the manifold to include a housing with the A, B, and C ports at 0°, 270°, and 180°, respectively.

Seated within the housing is a member that can rotate with respect to the housing. This member includes a lumen that undergoes a 90° turn inside the member, such that the entry and exit points of the lumen are a fixed radial distance away from each other. The member is positioned within the housing such that the entry and exit points align with ports A and B on the housing. For example, the member may be rotated counter-clockwise within the housing 90° to connect ports B and C such that they are in fluid communication. As ports A and C are 180° away from each other, this embodiment of the manifold will never be able to realize a flow path between ports A and C. The proximal end of an extension line may connect to port C of the two-way manifold, and the line itself may exit the housing through an appropriately sized port and terminate in a connecting element outside of the housing.

For example, the distal end of the extension line may terminate in a male Luer fitting. This Luer fitting may be closed with an appropriate cap (e.g., a non-vented, female, Luer cap). The proximal end of a second extension line may connect to port B of the two-way manifold, and the line itself may exit the housing through a second appropriately sized port and terminate in a connecting element. For example, the distal end of the extension line may terminate in a female Luer fitting that is joined to the distal end of the suspension syringe.

The system permits flow between the suspension syringe and the receiving syringe when the two-way manifold is positioned to permit flow between ports A and B. If a user or operator wishes to mix the contents of the suspension syringe, the user may depress the plunger of the suspension syringe, directing the EVOH/DMSO/tantalum mixture through the second extension line, out of port A of the two-way manifold, through the mixing component of the invention, and into the receiving syringe. As the receiving syringe is filled, the syringe plunger of the receiving syringe translates proximally, compressing the spring against the proximal wall of the housing. The potential energy in the spring is stored as long as the user maintains adequate pressure on the syringe plunger of the suspension syringe.

If the user removes pressure from the syringe plunger of the suspension syringe, the spring acts to release its potential energy and to apply pressure to the syringe plunger of the receiving syringe, driving the EVOH/DMSO/tantalum mixture out of the receiving syringe barrel, through the mixing component, into port A of the two-way manifold, out of port B of the two way manifold, through the second extension line, and back into the suspension syringe. In this manner, the user may cycle and thereby mix the EVOH/DMSO/tantalum suspension through the mixing component by iteratively depressing and releasing the suspension syringe plunger.

When the EVOH/DMSO/tantalum mixture has been adequately homogenized, the user may release the suspension syringe plunger, allow the suspension syringe to fill with the homogenized EVOH/DMSO/tantalum mixture, turn the two-way manifold such that ports B and C are in fluid communication, and depress the suspension syringe plunger to deliver the EVOH/DMSO/tantalum mixture out of the suspension syringe, through the second extension line, out of port C of the two-way manifold, and into the first extension line (provided the optional cap on the first extension line has been removed). This may be done to prime the system (i.e., to ensure that no air is resident within the fluid pathway of the system) prior to connecting the distal end of the first extension to the hub of a DMSO-compatible catheter.

Once primed and connected, this embodiment of a system of the invention may be used to mix and deliver and EVOH/DMSO/tantalum mixture to a patient undergoing an embolization procedure. If, during the course of the procedure, the physician operator wishes to further mix or remix the DMSO/EVOH/tantalum suspension (e.g., if the procedure has a protracted procedure time and there may be settling of the tantalum in the suspension), the physician operator may adjust the two-way manifold to permit flow between ports A and B, perform as many passes of the remaining DMSO/EVOH/tantalum suspension as desired to remix the suspension, then adjust the two-way manifold an additional time to permit flow between ports B and C, and continue delivering the DMSO/EVOH/tantalum suspension to the hub of the DMSO-compatible catheter.

A system of this type may be provided to the physician operator in a primed state (e.g., all air entrained within the flow path of the invention may be removed during the manufacture of the system). Alternatively, the components described as being contained within the suspension syringe (EVOH, DMSO, and tantalum) may be housing in different system components. For example, the suspension syringe may contain the DMSO/EVOH solution and the receiving syringe may contain the micronized tantalum. In another example, the suspension syringe and receiving syringe may have equal or differing volumes of the DMSO/EVOH/tantalum suspension at the time of manufacture.

It should be clear to one of skill in the art that the size of the housing, the stiffness, length, coil diameter, and coil thickness of the spring, the length of the syringe plunger, and other system parameters may be adjusted to compensate for differences in the locations and/or volumes of the three components of the embolic mixture. While this example uses an EVOH/DMSO/tantalum suspension or mixture as an example, it should be clear to one of skill in the art that the systems and methods herein are applicable to other embolic agents such as polymeric microspheres including, but not limited to spherical or non-spherical polyvinyl alcohol beads, tris-acryl gelatin microspheres, and the like.

In accordance with another embodiment, a system is provided for delivering embolic material into a target location within a patient's body that includes a first chamber including a first piston movable between a retracted position and a discharge position adjacent a first port, the first chamber comprising a flowable embolic material therein; a first actuator coupled to the first piston for directing the first piston from the retracted position to the discharge position to deliver the flowable embolic material from the first chamber out the first port when the first piston is moved from the retracted position to the discharge position; a second chamber including a second piston movable between a retracted position and a discharge position adjacent a second port, the second piston biased to move towards the discharge position; a diverter communicating with the first and second ports, and comprising a second actuator for opening one of a first flow path communicating between the first and second ports and a second flow path communicating between the first port and an outlet of the diverter; and a mixing component communicating with the first flow path for mixing the embolic material as the embolic material flows between the first chamber and the second chamber.

In accordance with yet another embodiment, a method is provided for preparing an assembly containing embolic material that includes actuating an actuator to cause flowable embolic material to exit a first chamber of the assembly, pass along a first flow path through a mixing component to mix the embolic material and into a second chamber of the assembly; releasing the actuator, whereupon the embolic material automatically passes along the first flow path from the second chamber through the mixing component to further mix the embolic material and into the first chamber; after mixing the embolic material, opening a second flow path from the first chamber to an outlet of the assembly; and actuating the actuator to direct the mixed embolic material through the outlet.

In accordance with still another embodiment, a method is provided for delivering embolic material into a target location within a patient's body that includes a) actuating an actuator to cause flowable embolic material to exit a first chamber, pass along a first flow path through a mixing component to mix the embolic material and into a second chamber; b) releasing the actuator, whereupon the embolic material automatically passes along the first flow path from the second chamber through the mixing component to further mix the embolic material and into the first chamber; c) after mixing the embolic material, opening a second flow path from the first chamber to an outlet; and d) actuating the actuator to direct the mixed embolic material through the outlet into a patient's body to embolize the target location.

In accordance with another embodiment, a system is provided for delivering embolic material into a target location within a patient's body that includes a first chamber including a first piston movable between a retracted position and a discharge position adjacent a first port, the first chamber comprising a flowable embolic material therein; a second chamber including a second piston movable between a retracted position and a discharge position adjacent a second port; a diverter communicating with the first and second ports, and comprising a diverter actuator movable between a first position for opening a first flow path communicating between the first and second ports, a second position for opening a second flow path communicating between the first port and an outlet of the diverter, and a third position for opening a third flow path communicating between the second port and the outlet; a mixing component communicating with the first flow path; a first chamber actuator coupled to the first piston for directing the first piston from the retracted position to the discharge position, with the diverter actuator opening the first flow path, to cause the embolic material to exit the first chamber, pass along the first flow path through the mixing component to mix the embolic material and into the second chamber, thereby causing the second piston to move from the discharge position to the retracted position as the embolic material enters the second chamber; and a second chamber actuator coupled to the second piston for directing the second piston from the retracted position to the discharge position, with the diverter actuator opening the first flow path, to cause the embolic material introduced into the second chamber from the first chamber to exit the second chamber, pass along the first flow path through the mixing component to further mix the embolic material and into the first chamber, thereby causing the first piston to move from the discharge position to the retracted position as the embolic material enters the first chamber, wherein the diverter actuator is movable to one of the second position and the third position to open the second flow path or third flow path to deliver mixed embolic material from one of the first chamber and the second chamber out the outlet.

In accordance with still another embodiment, a method is provided for delivering embolic material into a target location within a patient's body that includes a) actuating a first chamber actuator to cause flowable embolic material to exit a first chamber, pass along a first flow path through a mixing component to mix the embolic material and into a second chamber; b) actuating a second chamber actuator to cause the embolic material to exit a second chamber, pass along a first flow path through a mixing component to further mix the embolic material and into a first chamber; c) after mixing the embolic material into one of the first and second chambers, opening a delivery path from the one of the first and second chambers to an outlet; and d) actuating one of the chamber actuators to direct the mixed embolic material through the outlet into a patient's body to embolize the target location.

Other aspects and features including the need for and use of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EXEMPLARY EMBODIMENTS

Before exemplary embodiments are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymer and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1A:
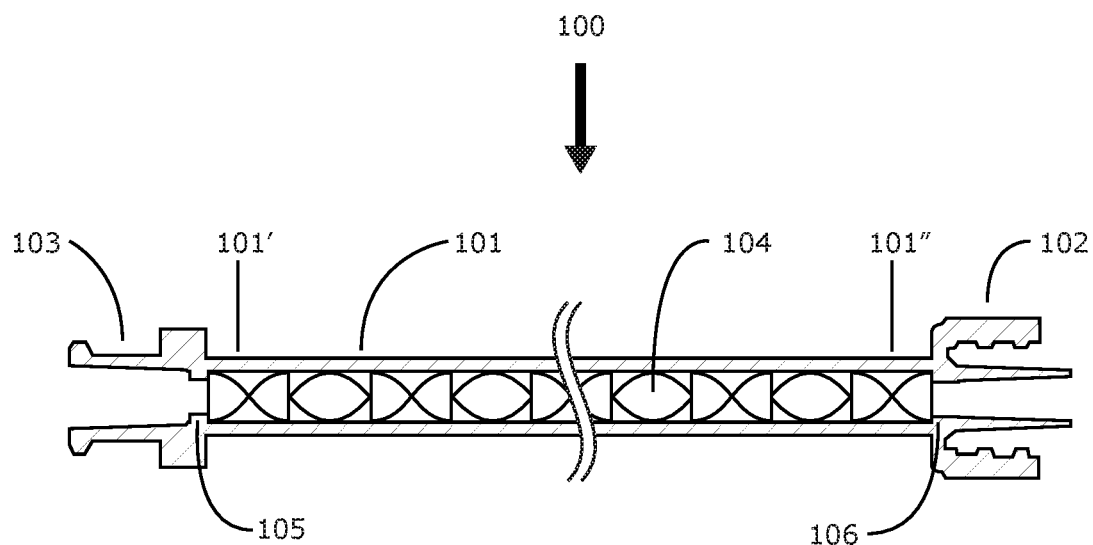
FIG. 1A shows a plan view of an exemplary embodiment of a mixing device including a proximal female Luer fitting and a distal male Luer fitting.

Turning to the drawings, FIG. 1A shows an exemplary embodiment of a mixing component 100 that may be included in the systems and methods herein. Generally, the mixing component 100 includes an elongate member 101 with proximal 101' and distal 101" ends, a distal male Luer fitting 102, a proximal female Luer fitting 103, and a series of helical static mixing elements 104. The elongate member 101 further includes a lumen sized to house helical static mixing elements 104 that is in fluid communication with the lumens of distal male Luer fitting 102 and proximal female Luer fitting 103, and internal features 105 and 106.

Internal features 105 and 106 are sized to interfere with helical static mixing elements 104 and prevent proximal or distal translation of the helical static mixing elements 104 with respect to the elongate member 101. Internal features 105 and 106 may be ring or flange-like in geometry and structure, or may be protrusions into the lumen of the elongate member 101 that are discrete and not continuous about the interior diameter of the elongate member. Optionally (not shown), the function of restricting the translation of the helical static mixing elements 104 may be served by a combination of a groove and O-ring set into the internal surface of elongate member 101 or other like mechanisms for obtaining a mechanical interference. For example, the outer diameter of the helical static mixing elements 104 may be chosen to press fit into the lumen of the elongate member 101 such that the helical static mixing elements 104 do not translate up to a given pressure of mixing materials flowing through the mixing component of the invention.

Figure 1B:
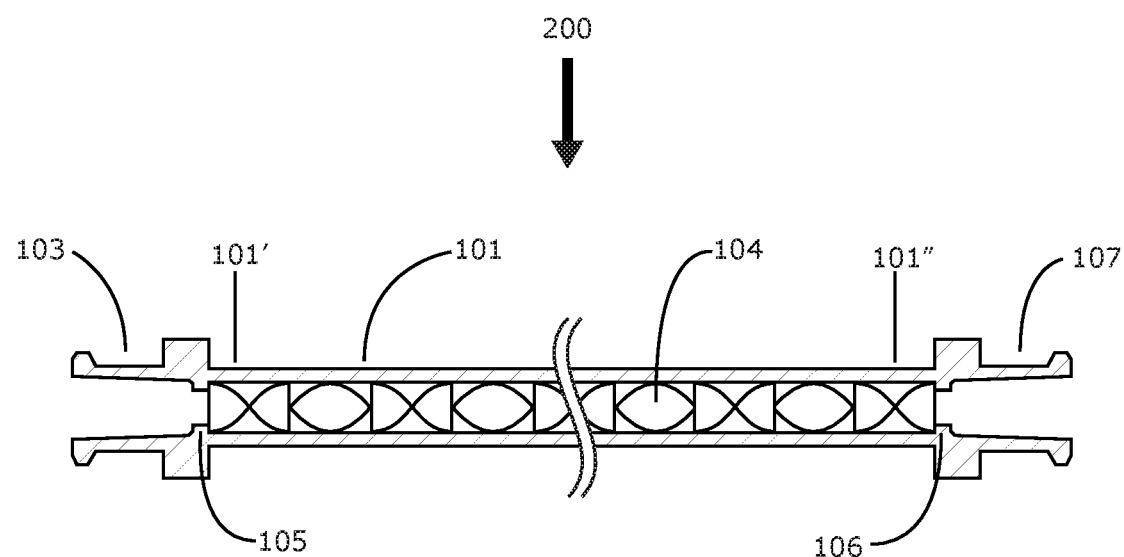
FIG. 1B shows a plan view of another exemplary embodiment of a mixing device including proximal and distal female Luer fitting.

While the exemplary mixing component shown in FIG. 1A includes a set of at least nine helical static mixing elements, it should be clear to one of skill in the art that a lesser number of static mixing elements maybe used in the systems and methods herein. Furthermore, the connecting elements of this embodiment are not restricted to male and female Luer fittings; any combination of connecting elements may be employed to reversibly or irreversibly join the mixing component to other devices, injection lines, catheters, manifolds, and the like. Similarly, while the example of FIG. 1A includes helical static mixers housed in a tubular elongate member, it should be clear to one of skill in the art that other geometries of static mixing elements and the corresponding geometries of the elongate member may be provided. For example, FIG. 1B shows another embodiment of a mixing component 200 that is generally similar to mixing component 100 other than the replacement of the distal male Luer fitting 102 with a distal female Luer fitting 107.

Figure 2A:
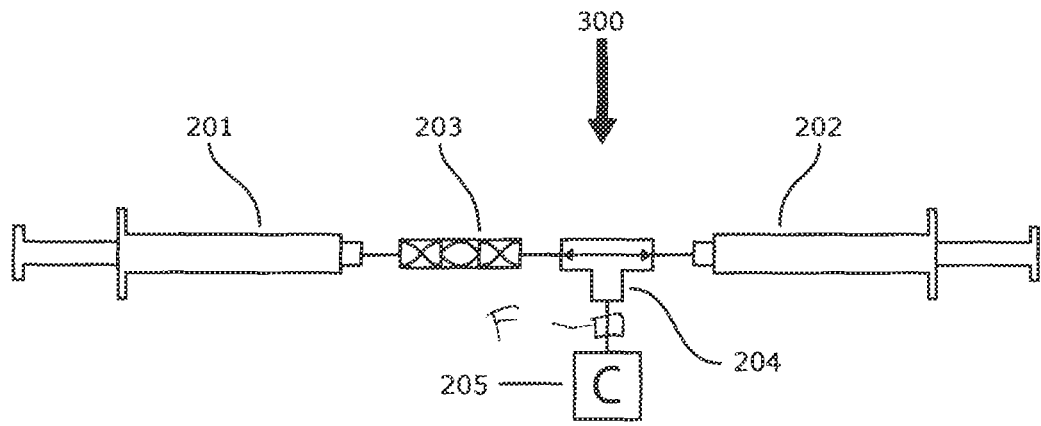
FIGS. 2A-2C are schematic illustrations of an exemplary embodiment of a system for delivering an embolic material in three different flow states.
Figure 2B:
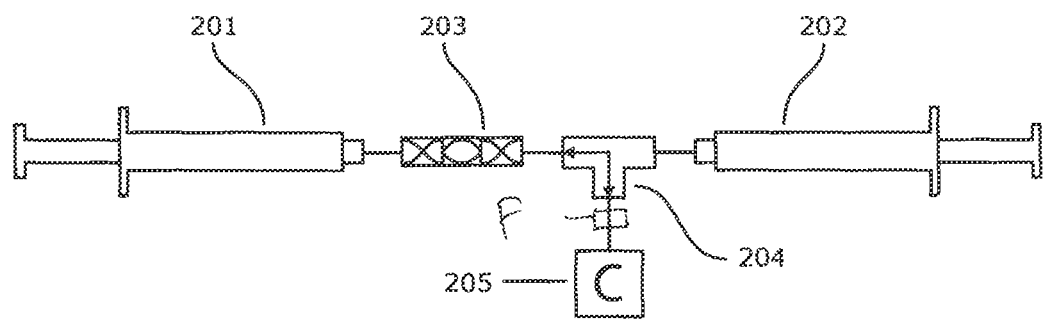
Figure 2C:
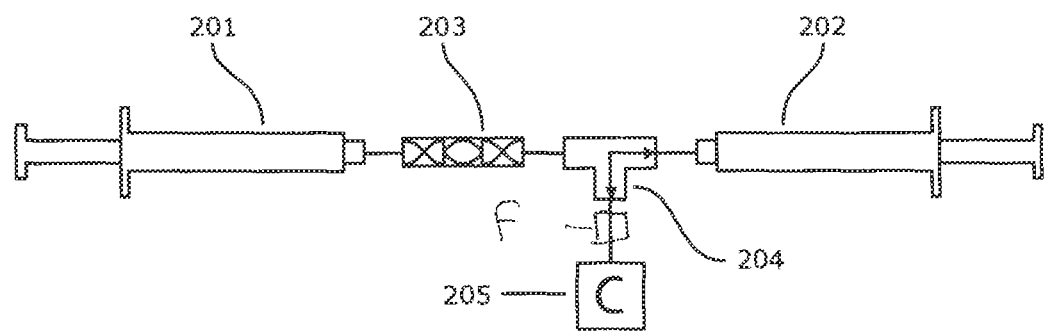

FIGS. 2A-2C show schematic views of an exemplary embodiment of a system 300 for delivering embolic material in three different flow states during different stages of using the system 300. Generally, the system 300 includes a suspension or first syringe 201 containing a liquid embolic suspension (not shown), an initially empty receiving or second syringe 202, a mixing component 203, a three-way stopcock or other diverter 204, and a catheter 205 that is compatible with the liquid embolic suspension. The suspension syringe 201 is connected to the mixing component 203, which is in turn connected to the three-way stopcock 204. The remaining two arms of the three-way stopcock 204 are connected to the receiving syringe 202 and the catheter 205. While FIGS. 2A-2C show the mixing component 203 positioned between the suspension syringe 201 and three-way stopcock 204, in an alternative arrangement, the mixing component 203 may be positioned between the receiving syringe 202 and three-way stopcock 204 (not shown).

FIG. 2A illustrates a flow state of the system with the stopcock 204 in an initial position wherein the suspension syringe 201 and receiving syringe 202 are in fluid communication with each other, and flow to the catheter 205 is prevented. With the system 300 in this flow state, the liquid embolic suspension may be passed from the suspension syringe 201 through the mixing component 203 and the stopcock 204 to the receiving syringe 202 and vice versa. The passage of the liquid embolic suspension from syringe to syringe may homogenize the suspension and/or otherwise prepare the suspension for delivery into a patient's body, e.g., into a body lumen or other target location, as described elsewhere herein. Once a desired amount of mixing is accomplished, and depending on which of the two syringes contains the homogenized suspension, the liquid embolic may be directed to the catheter 205 by positioning the stopcock 204 to a delivery position, as shown in FIG. 2B or FIG. 2C.

FIG. 2B is a schematic with the stopcock 204 positioned such that flow is permitted between the suspension syringe 201 and the catheter 205, and would be appropriate when the desired amount of mixing is obtained with the last pass of the liquid embolic suspension (i.e., between the suspension syringe 201 and the receiving syringe 202 as shown in FIG. 2A) placing the liquid embolic suspension in the suspension syringe 201. FIG. 2C is a schematic with the stopcock 204 positioned such that flow is permitted between the receiving syringe 202 and the catheter 205, and would be appropriate when the desired amount of mixing is obtained with the last pass of the liquid embolic suspension (i.e., between the suspension syringe 201 and the receiving syringe 202 as shown in FIG. 2A) placing the liquid embolic suspension in the receiving syringe 202.

In an alternative embodiment, the system 200 may include an in-line filter F positioned between the stopcock 204 and the catheter 205, e.g., as shown in FIGS. 2A-2C. The in-line filter may be chosen to vent entrained air from the mixed liquid embolic suspension, screen out particulate or other potential contaminants above a specific size, and like prior to the suspension passing down the catheter 205 and into the patient's body. It should also be clear to one of skill in the art that other diverter mechanisms for controlling flow other than the three-way stopcock 204 shown in FIGS. 2A-2C may be provided, if desired.

Figure 3A:
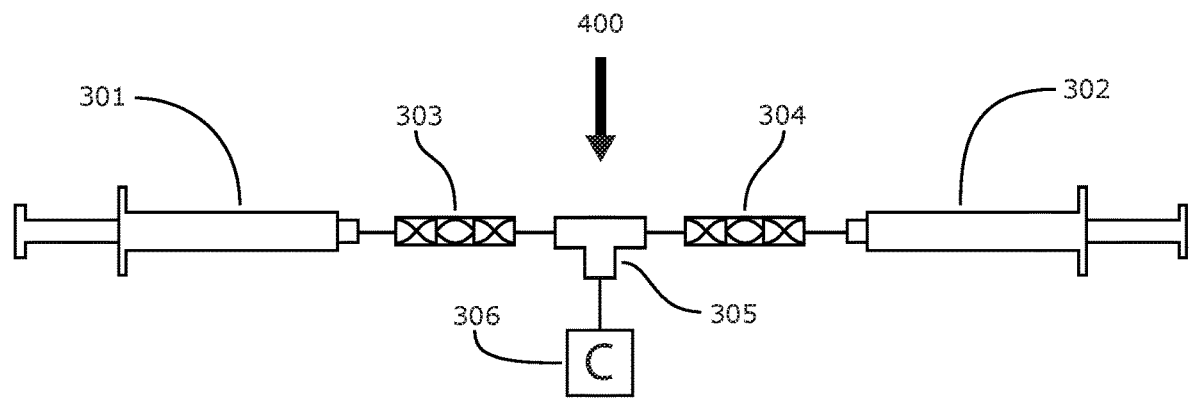
FIG. 3A is a schematic illustration of another exemplary system for delivering embolic material including two mixing components.

Turning to FIG. 3A, a schematic illustration of another system 400 is shown that includes a suspension or first syringe 301 containing the liquid embolic suspension (not shown), an initially empty receiving or second syringe 302, a first mixing component 303, a second mixing component 304, a three-way stopcock or other diverter 305, and a catheter 306 that is compatible with the liquid embolic suspension. The principles of operation of the system are similar to those described for FIGS. 2A-2C. It should be noted that although mixing components 303 and 304 are represented by the same symbol in FIG. 3A, the individual mixing components 303 and 304 are not required to be identical and may include any of the mixing elements described elsewhere herein, e.g., including a plurality of helical elements and/or flow dividers arranged sequentially within a tubular housing. Differences in diameter, length, number and size of mixing elements, structure and geometry of the mixing elements and elongate members, materials of construction, and the like are all contemplated.

Optionally, in an alternative embodiment, the system 400 (not shown) may include an in-line filter positioned between three-way stopcock 305 and the catheter 306 and/or in line between each of the syringes 301, 302 and the stopcock 305. The in-line filter may be chosen to vent entrained air from the mixed liquid embolic suspension, screen out particulate or other potential contaminants above a specific size, and like prior to the suspension passing down the catheter 306 and into the patient's body. It should also be clear to one of skill in the art that other diverter mechanisms for controlling flow other than the three-way stopcock 305 may be provided.

Figures 3B, 3C:
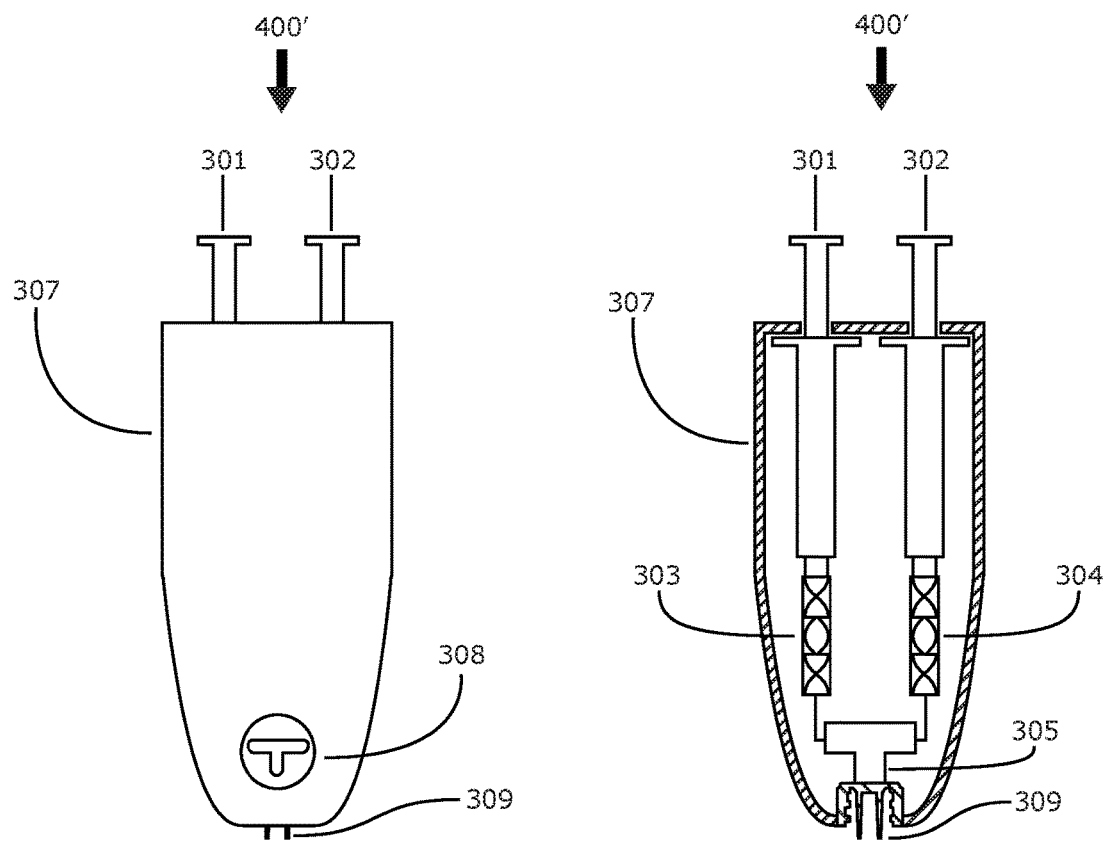
FIG. 3B shows a top view of the system of FIG. 3A enclosed within a housing.
FIG. 3C shows a cross-sectional view of the system of FIG. 3B.

Turning to FIGS. 3B and 3C, an exemplary embodiment of a system 400' is shown that includes components generally similar to the system 400 except enclosed within a housing 307 and including a male Luer fitting 309 connected to stopcock 305. The housing 307 may be contoured to ergonomically fit the physician operator's hand and/or provide intuitive access to and operation of suspension syringe 301, receiving syringe 302, and three-way stopcock 305. This may be accomplished through the use of an actuator such as a knob 308 that connects to the three-way stopcock 305 and provides information to the operator about the state of stopcock 305 through markings, inscriptions, labels, tactile feedback, audible feedback, combinations thereof, and the like.

Figure 4:
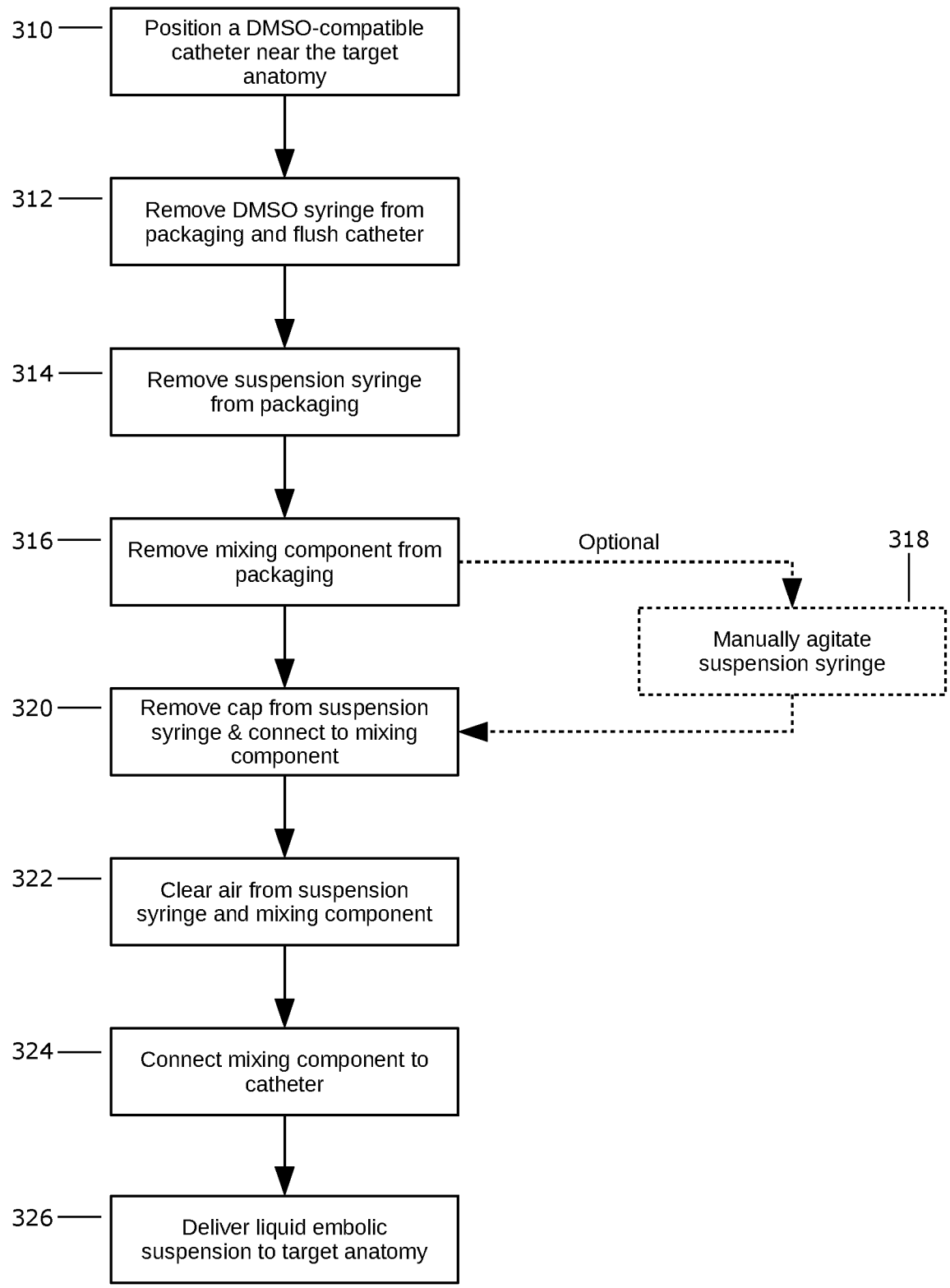
FIG. 4 is a flowchart illustrating an exemplary method for using a system including a capped syringe containing pure DMSO, a capped syringe containing a mixture of EVOH, DMSO, and tantalum, and a mixing component.

Turning to FIG. 4, a flowchart shows an exemplary embodiment of a method for using a system to deliver embolic material that includes a syringe containing pure DMSO, a suspension syringe containing a suspension of tantalum in a solution of DMSO and EVOH, and a mixing component (not shown). As a first step 310, a physician operator or other user may position a DMSO-compatible catheter near a target location within a patient's body, e.g., an aneurysm, cavity, or other body lumen (not shown), using standard fluoroscopic and/or magnetic guidance techniques. Then, at step 312, the physician operation then takes the syringe containing pure DMSO out of any provided packaging using sterile technique and flushes the catheter, positioned with the patient's body, with pure DMSO. This acts to prevent premature precipitation of the EVOH in the suspension syringe due to backflow of blood or saline up the lumen of the catheter from the body lumen. At steps, 314 and 316, the suspension syringe and mixing component are removed from their provided packaging. Optionally, at step 318, the suspension syringe may be manually agitated, e.g., to coarsely pre-mix the EVOH/DMSO/tantalum suspension. Then at step 320, a cap is then removed from the suspension syringe and the suspension syringe is connected to the mixing component.

Then at step, 322, the assembly of the suspension syringe and mixing component may be held vertically such that the distal end of the mixing component is oriented upwards and the syringe plunger is depressed until the suspension fills the mixing component and all air is cleared from the assembly.

In addition or alternatively, other techniques known to the art for purging air from medical devices and equipment may optionally be used in place or in addition to the described technique, including the use of an in-line air-venting filter such as an intravenous filter (not shown).

Then at step 324, the distal end of the mixing component is then connected to the hub of the catheter and the liquid embolic may be delivered into the target location, at step 326. The presence of the mixing component between the suspension syringe and the catheter hubs enables in-line mixing and homogenization of the liquid embolic suspension. While this example uses an EVOH/DMSO/tantalum suspension or mixture as an example, it should be clear to one of skill in the art that this method is applicable to other embolic agents, such as polymeric microspheres including, but not limited to spherical or non-spherical polyvinyl alcohol beads, tris-acryl gelatin microspheres, and the like.

Figure 5:
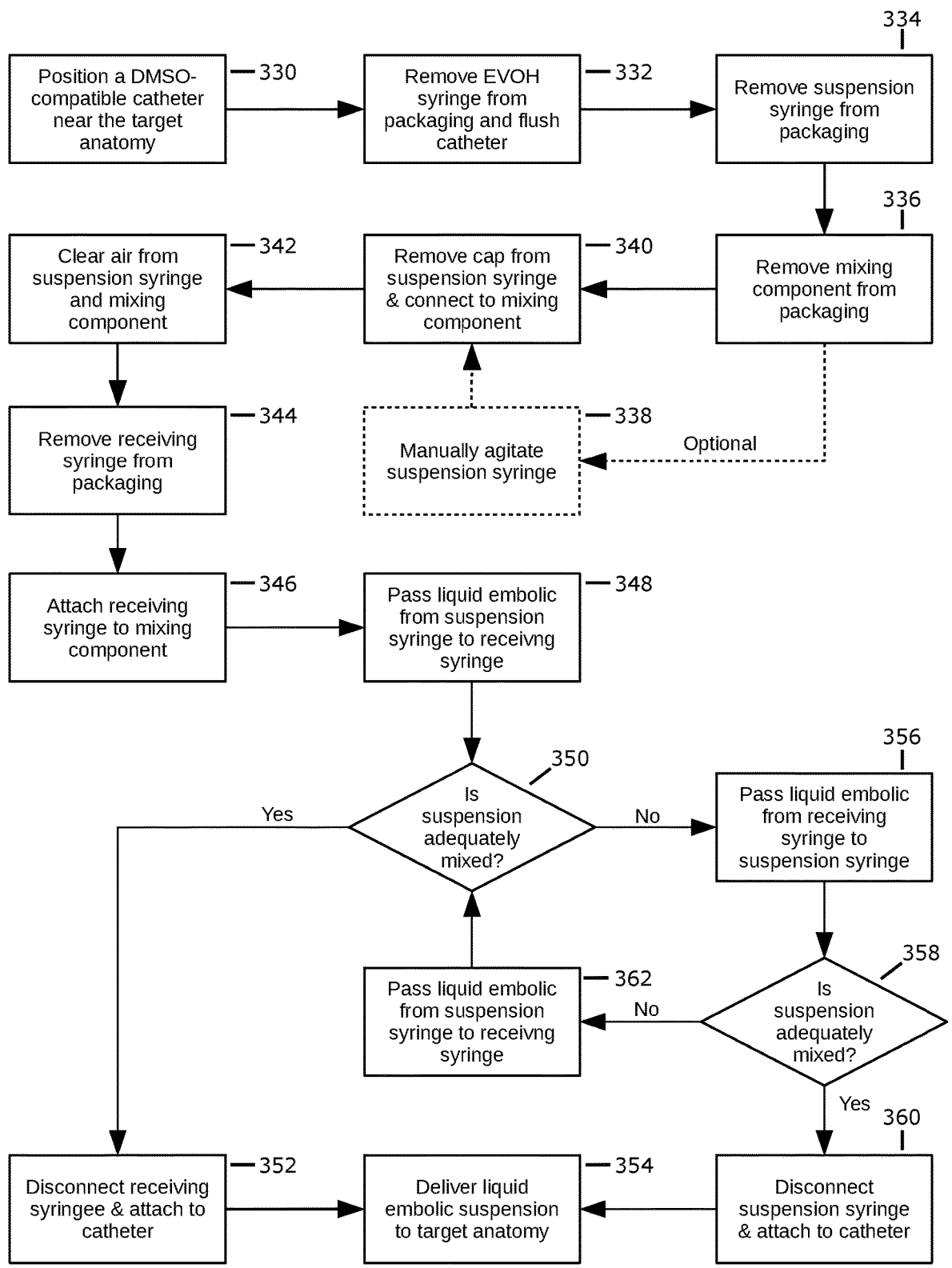
FIG. 5 is a flowchart illustrating an exemplary method for using a system including a capped syringe containing pure DMSO, a receiving syringe, a capped syringe containing a mixture of EVOH, DMSO, and tantalum, and a mixing component.

Turning to FIG. 5, a flowchart shows another exemplary method for using a system to deliver embolic material including a syringe containing pure DMSO, a suspension syringe containing a suspension of tantalum in a solution of DMSO and EVOH, an empty receiving syringe, and a mixing component (not shown). As a first step 330, the physician operator positions a DMSO-compatible catheter near the target location within a patient's body, e.g., using standard fluoroscopic or magnetic guidance techniques. Then at step 332, the physician operation then takes the syringe containing pure DMSO out of the provided packaging using sterile technique and flushes the catheter with pure DMSO. This acts to prevent premature precipitation of the EVOH in the suspension syringe due to backflow of blood or saline up the lumen of the catheter. At steps 334, 336, the suspension syringe and mixing component are removed from the provided packaging, and, optionally, the suspension syringe may be manually agitated to coarsely pre-mix the EVOH/DMSO/tantalum suspension at step 338.

Then at step 340, the cap is then removed from the suspension syringe and the suspension syringe is connected to the mixing component. At step 342, the assembly of the suspension syringe and mixing component may be held vertically such that the distal end of the mixing component is oriented upwards and the syringe plunger is depressed until the suspension fills the mixing component and air is cleared from the assembly. Other techniques known to the art for purging air from medical devices and equipment may optionally be used in place or in addition to the described technique. At step 344, the receiving syringe is then removed from the provided packaging and connected to the distal end of the mixing component at step 346.

Then, at step 348, the plunger of the suspension syringe is then depressed to pass the liquid embolic suspension through the mixing component to the receiving syringe. If, at step 350, the liquid embolic suspension is adequately mixed, the receiving syringe is disconnected from the mixing component and connected to the hub of the catheter at step 352, and the liquid embolic may be delivered into the target location at step 354. However, if at step 350, the liquid embolic suspension is not adequately mixed after the single pass from the suspension syringe to the receiving syringe, at step 356, the plunger of the receiving syringe may be depressed to pass the liquid embolic suspension through the mixing component to the suspension syringe.

Thereafter, at step 358, if the liquid embolic suspension is adequately mixed, the suspension syringe is disconnected from the mixing component and connected to the hub of the catheter at step 360, and the liquid embolic may be delivered to the target location at step 354. If not, at step 362, the liquid embolic suspension may be passed from the suspension syringe back to the receiving syringe. The loop including steps 356 and 362 of passing the liquid embolic suspension between the suspension syringe and the receiving syringe may be repeated for as many passes as needed or desired to adequately mix the liquid embolic suspension.

Optionally, an in-line air-venting filter, such as an intravenous filter (not shown), may be placed proximal to the hub of the catheter, e.g., to remove any entrained air and/or other undesired particulate from the suspension prior to entering the patient. In addition or alternatively (again not shown), the physician operator may choose to remove the syringe containing the mixed embolic suspension along with the mixing component and connect the free end of the mixing component to the hub of the catheter or in-line filter. This may allow for a final pass of the liquid embolic suspension through the static mixer immediately prior to being administered to the patient. While this example uses an EVOH/DMSO/tantalum suspension or mixture as an example, it should be clear to one of skill in the art that this method is applicable to other embolic agents such as polymeric microspheres including, but not limited to spherical or non-spherical polyvinyl alcohol beads, tris-acryl gelatin microspheres, and the like.

Figure 6:
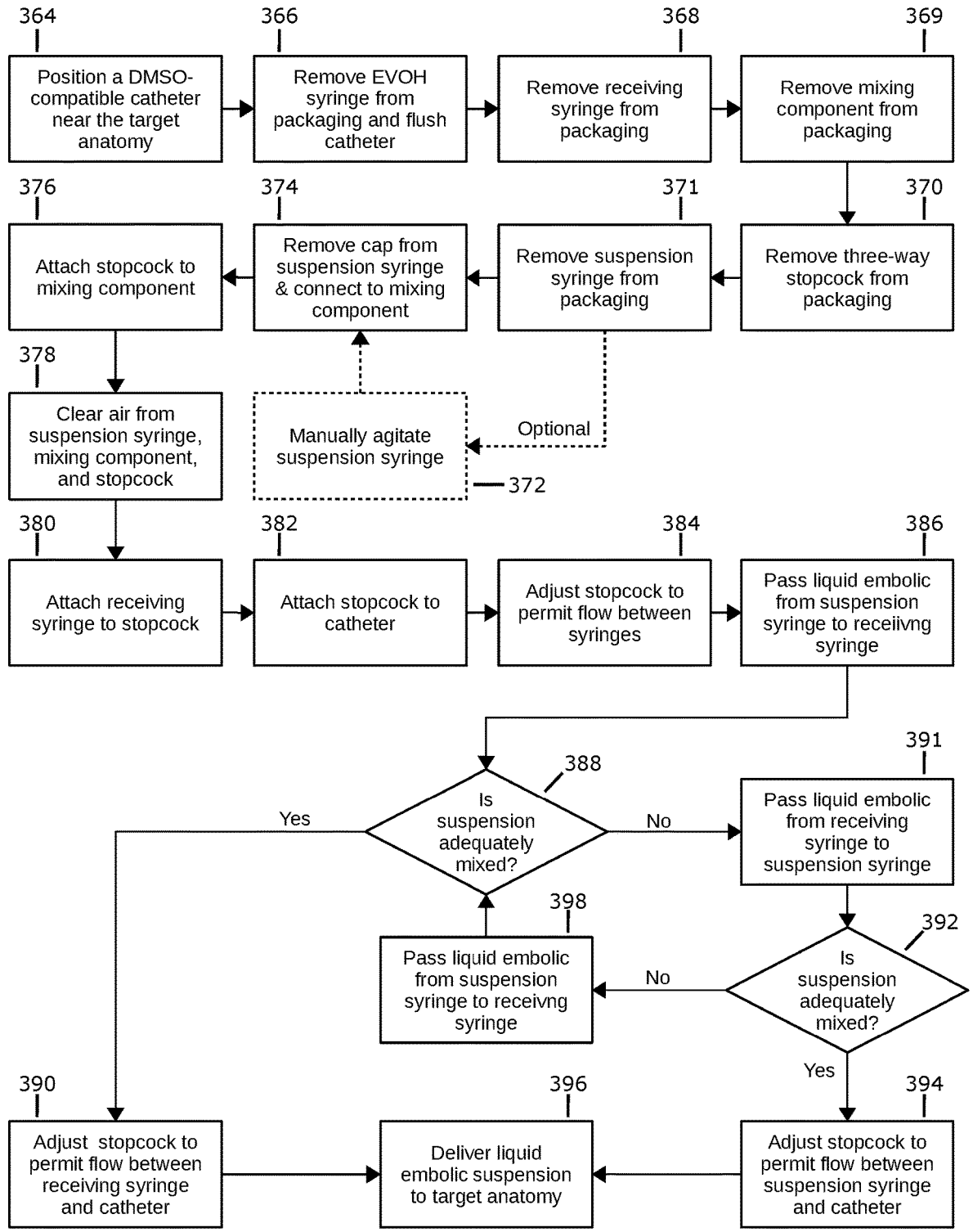
FIG. 6 is a flowchart illustrating an exemplary method for using a system including a capped syringe containing pure DMSO, a receiving syringe, a capped syringe containing a mixture of EVOH, DMSO, and tantalum, a three-way stopcock, and a mixing component.

Turning to FIG. 6, a flowchart shows still another exemplary embodiment of a method for using a system to deliver embolic material that includes a syringe containing pure DMSO, a suspension syringe containing a suspension of tantalum in a solution of DMSO and EVOH, an empty receiving syringe, a mixing component, and a three-way stopcock (not shown). As a first step 364, the physician operator positions a DMSO-compatible catheter near a target location within a patient's body, e.g., using standard fluoroscopic or magnetic guidance techniques. Then, at step 366, the physician operation then takes the syringe containing pure DMSO out of the provided packaging using sterile technique and flushes the catheter with pure DMSO. This acts to prevent premature precipitation of the EVOH in the suspension syringe due to backflow of blood or saline up the lumen of the catheter. In steps 368-371, the suspension syringe, mixing component, three-way stopcock, and receiving syringe are removed from the provided packaging. Optionally, at step 372, the suspension syringe may be manually agitated, e.g., to coarsely pre-mix the EVOH/DMSO/tantalum suspension, similar to other embodiments herein.

Then, at steps 374 and 376, the cap is removed from the suspension syringe and the suspension syringe is connected to the mixing component, and the free end of the mixing component is connected to the three-way stopcock. At step 378, the assembly of the suspension syringe, mixing component and stopcock is held vertically such that the free ends of the three way stopcock are oriented upwards and the syringe plunger is depressed until the suspension fills the mixing component and stopcock, and all air is cleared from the assembly. Other techniques known to the art for purging air from medical devices and equipment may optionally be used in place or in addition to the described technique.

Then, at steps 380 and 382, the receiving syringe is then connected to one of the free arms of the three-way stopcock and the hub of the catheter is connected to the remaining free arm of the three-way stopcock. At step 384, the three-way stopcock is adjusted to permit flow between the suspension syringe and the receiving syringe, and, at step 386, the plunger of the suspension syringe is depressed to pass the liquid embolic suspension through the mixing component to the receiving syringe.

At step, 388, if the liquid embolic suspension is adequately mixed, the three way stopcock is adjusted to permit flow between the receiving syringe at step 390, and the hub of the catheter and the liquid embolic may be delivered to the target location, at step 396. However, at step 391, if the liquid embolic suspension is not adequately mixed after the single pass from the suspension syringe to the receiving syringe, the plunger of the receiving syringe may be depressed to pass the liquid embolic suspension through the mixing component to the suspension syringe. At step 392, if the liquid embolic suspension is adequately mixed, the three-way stopcock is adjusted to permit flow between the suspension syringe and the hub of the catheter at step 394, and the liquid embolic may be delivered to the target anatomy at step 396. If not, at step 398, the liquid embolic suspension may be passed from the suspension syringe back to the receiving syringe.

Optionally, the loop including steps 391 and 398 of passing the liquid embolic suspension between the suspension syringe and the receiving syringe may be repeated for as many passes as needed or desired to adequately mix the liquid embolic suspension. Additionally or alternatively, an in-line air-venting filter, such as an intravenous filter (not shown), may be placed between the three-way stopcock and the hub of the catheter to remove any entrained air or other undesired particulate from the suspension prior to entering the patient. While this example uses an EVOH/DMSO/tantalum suspension or mixture as an example, it should be clear to one of skill in the art that this method is applicable to other embolic agents such as polymeric microspheres including, but not limited to spherical or non-spherical polyvinyl alcohol beads, tris-acryl gelatin microspheres, and the like.

Figure 7A:
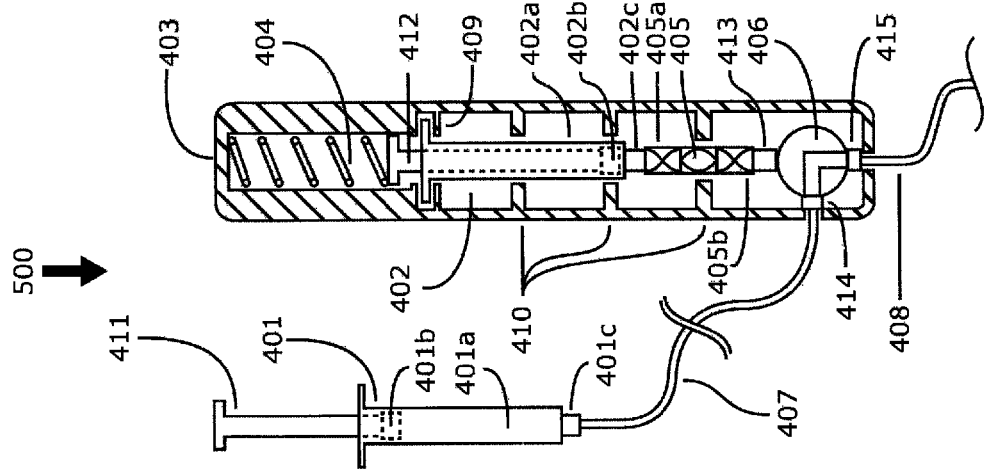
FIGS. 7A-7C are cross-sectional views of an exemplary system for delivering an embolic material, showing three phases of operation of the system.
Figure 7B:
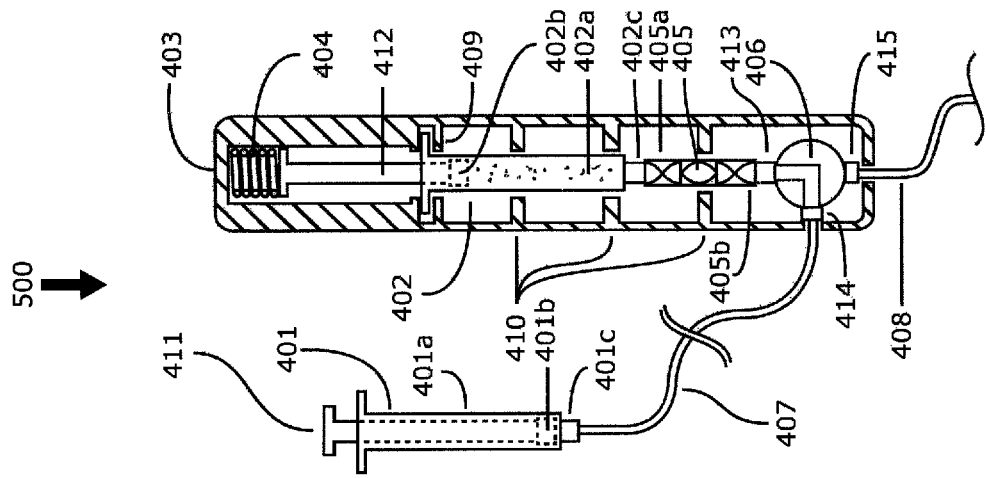
Figure 7C:
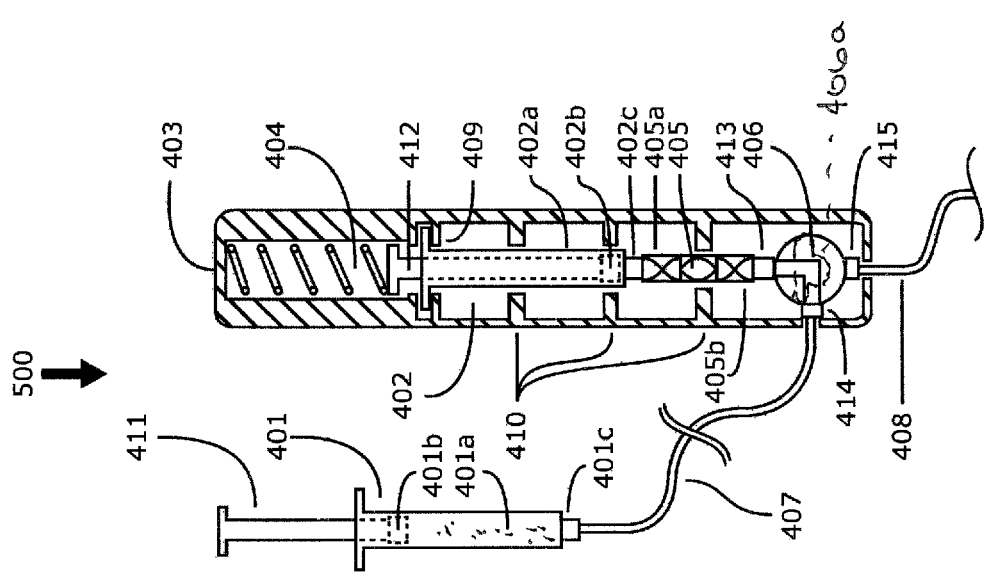

Turning to FIGS. 7A-7C, another exemplary embodiment of a system 500 for preparing and delivering embolic material is shown that generally includes a suspension or first syringe 401 defining a first chamber therein containing a liquid embolic suspension (represented by dots in first chamber 401a), a receiving or second syringe 402 defining a second chamber, a housing 403, a spring 404, a mixing component 405, a two-way manifold 406, a first extension line 407, and a second extension line 408. The housing 403 may include one or more retaining flanges or mounting features, such as retaining flanges 409 and 410, for containing and/or limiting movement of internal components, e.g., the spring 404, receiving syringe 402, and mixing component 405 contained within the housing 403.

Generally, each syringe 401, 402 includes a barrel defining an interior chamber 401a, 402a, a piston 401b, 402b slidably disposed within the barrel, which are coupled to respective plungers 411, 412, and a port 401c, 402c communicating with the chamber 401a, 402a. The first piston 401b is movable within the first chamber 401a between a proximal or retracted position, e.g., as shown in FIGS. 7A and 7C and a distal or discharge position, e.g., as shown in FIG. 7B. Similarly, the second piston 402b is movable within the second chamber 402a between a distal or discharge position, e.g., as shown in FIGS. 7A and 7C and a proximal or retracted position, e.g., as shown in FIG. 7B. Alternatively, the first plunger 411 and piston 401b may be a singular unit (e.g., as in a glass syringe). Similarly, the second plunger 412 and piston 402b may be a singular unit (e.g., as in a glass syringe) as well.

The spring 404 may be configured to bias the second piston 402b to the distal position shown in FIGS. 7A and 7C. In an exemplary embodiment, the spring 404 may be a compression spring mounted within the housing 403 proximal to the second plunger 412 to bias the second plunger 412 (and second piston 402b) distally, yet may be resiliently compressed to allow the second plunger 412 (and second piston 402b) to move proximally during use of the system 500, as described further elsewhere herein. For example, the spring 404 may be assembled within the housing 403 in a fully relaxed or unloaded condition or alternatively, the spring 404 may be assembled in a partially compressed state providing some amount of preload to the receiving syringe plunger 412. Such spring preload may ensure that the receiving syringe plunger 412 returns to its fully depressed or distal position, ensuring that substantially all of the liquid embolic suspension is automatically returned to the suspension syringe 401, as described elsewhere herein.

The flanges 409 and 410 maintain the relative position of the internal components parts with respect to each other within the housing 403. For example, as shown, the flanges 409 are sized and located to create a space for finger flanges or wings of the receiving syringe 402 and/or otherwise engage the barrel of the receiving syringe 402 to prevent movement. The placement of the receiving syringe 402 in between the flanges 409 of the housing 403 provides space for the spring 404 proximal to the proximal end of the receiving syringe plunger 412. The spring 404 and proximal end of the plunger 412 may be sized such that the spring 404 may engage the proximal end to direct the plunger 412 (and piston 402b) distally. FIG. 7A shows the spring in a neutral or low energy state, e.g., neither in tension or compression or subject only to the initial preload.

The port 402c of the receiving syringe 402 is connected, either directly or through a supplemental extension line (not shown), to a proximal end 405a of the mixing component 405. A distal end 405b of the mixing component 405 is connected, either directly or through another supplemental extension line (not shown), to the two-way manifold 406. For example, the two-way manifold 406 may include three ports, e.g., a first or middle port 414, e.g., mounted to or communicating outside the housing 403, e.g., to the first port 401c of the suspension syringe 401 via flexible tubing 407, a second or proximal port 413 communicating with the distal end 405b of the mixing component 405, and a third or distal port 415 also mounted to or communicating outside the housing 403, e.g., to an outlet at a distal end of the housing 403, e.g., for communicating with a catheter or other tubular member or delivery device (not shown), as described further elsewhere herein.

FIG. 7A shows the two-way manifold 406 in a first configuration that defines a flow path between the proximal port 413 and middle port 414, i.e., a first flow path between the first chamber 401a and second chamber 402a, while FIG. 7C shows the two-way manifold 406 in a second configuration that defines a flow path between the middle port 414 and the distal port 415, i.e., a second flow path between the first chamber 401a and the outlet of the housing 403. The two-way manifold 406 may include a knob, dial, or other actuator, e.g., knob 406a shown in phantom in FIG. 7A, configured to rotate the two-way manifold 406 between the first and second configurations, e.g., similar to a two-position or two-way stopcock. The middle port 414 of the two-way manifold 406 is connected to the first extension line 407, which is, in turn connected to the suspension syringe 401. The distal port 415 of the two-way manifold 406 is connected to a second extension line 408. Both extension lines 407 and 408 exit the housing 403 through openings in the body of the housing 403 or are coupled to connectors (not shown) provided on the outer wall of the housing 403.

In one example, initially, the suspension syringe 401 shown in FIG. 7A may be filled with the majority of the volume of the liquid embolic suspension, i.e., with the first piston 401b in the proximal position, and the receiving syringe 402 may be substantially empty, i.e., with the second piston 402b in the distal position. FIG. 7B depicts a state of the system 500 in which the suspension syringe plunger 411 has been fully depressed, e.g., manually by a user, driving substantially all of the liquid embolic suspension out the first port 401c, through the extension line 407, the two-way manifold 406, the mixing component 405, and into the chamber 402a of the receiving syringe 402. This, in turn, causes the receiving syringe plunger 412 and second piston 402b to translate proximally and compress the spring 404 as the second chamber 402a fills with liquid embolic suspension.

The spring 404 will remain compressed as long as the force applied to the suspension syringe plunger 411 exceeds the spring force generated by the compression of spring 404, e.g., by the user continuing to press on the first plunger 411. If the force on the suspension syringe plunger 411 is removed, the spring 404 will expand towards its relaxed position, pushing the liquid embolic suspension back out of the second chamber 402a, through the port 402c, the mixing component 405, the two-way manifold 406, the extension line 407, and into the chamber 401a of the suspension syringe 401 and the system will return to the state depicted in FIG. 7A. The reciprocating process of transferring the liquid embolic suspension back and forth between the suspension syringe 401 and receiving syringe 402 and through mixing component 405 serves to mix and homogenize the liquid embolic suspension.

Once this process has been completed to the satisfaction of the user and adequate mixing is achieved, the user may allow the mixed liquid embolic suspension to return to the suspension syringe 401 and then turn the two-way manifold 406 to the second configuration such that the middle port 414 and distal port 415 are in fluid communication as shown in FIG. 7C. In this state, depression of the suspension syringe plunger 411 will direct the mixed liquid embolic suspension along the second flow path, i.e., out the port 401c, through the extension line 407, the two-way manifold 406, and out of the second extension line 408. This may be done to prime the second extension line 408 in preparation for connecting the second extension line 408 to, for example, a catheter compatible with the liquid embolic suspension (not shown). Alternatively, the second extension line 408 may be omitted and replaced by a connector or other mechanism (e.g., a male rotating Luer-lock fitting) for connecting directly to a proximal end of the catheter.

For example, the catheter (not shown) may include a proximal end, e.g., including a handle or hub that includes a port connectable to the second extension line 408 or directly to the housing 403, a distal end sized for introduction into a patient's body, and a lumen extending between the proximal and distal ends that communicates with the second flow path to deliver the mixed liquid embolic suspension beyond the distal end. The distal end may be introduced into the patient's body using conventional methods, e.g., percutaneously to access the patient's vasculature via a guidewire and/or access sheath, and advanced to a target location being embolized.

The user may then proceed with delivering the liquid embolic suspension to the target location. If at any time, the user perceives a need to further mix the liquid embolic suspension (e.g., if the suspension begins to settle during the course of a long procedure), the user may return the two-way manifold 406 to the configuration shown in FIGS. 7A and 7B (wherein the proximal port 413 and middle port 414 are in fluid communication) and repeat the process of passing the liquid embolic suspension along the first flow path through the mixing component 405 and between the suspension 401 and receiving 402 syringes to obtain additional mixing and homogenization of the liquid embolic suspension. Once the embolic suspension has been delivered, the catheter may be directed to one or more locations to embolize other locations and/or removed using conventional methods.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for delivering a flowable embolic material into a target location within a body of a patient, comprising:
 a first chamber including a first piston movable between a retracted position and a discharge position adjacent a first port, the first chamber comprising the flowable embolic material therein;
 a first actuator coupled to the first piston for directing the first piston from the retracted position of the first piston to the discharge position of the first piston to deliver the flowable embolic material from the first chamber out the first port when the first piston is moved from the retracted position of the first piston to the discharge position of the first piston;
 a housing sized to be held in a hand of a user;
 a barrel mounted within an interior of the housing including a second chamber including a second piston movable between a retracted position and a discharge position adjacent a second port, the second piston biased to move towards the discharge position of the second piston;
 a diverter mounted within the interior of the housing adjacent the barrel and communicating with the first port and the second port, the diverter comprising a second actuator for opening one of a first flow path communicating between the first port and the second port or a second flow path communicating between the first port and an outlet of the diverter; and
 a mixing component communicating with the first flow path for mixing the flowable embolic material as the flowable embolic material flows between the first chamber and the second chamber, wherein the mixing component includes an elongate member mounted within the interior of the housing, the elongate member comprising a proximal end and a distal end and a lumen housing a series of static mixing elements that mixes the flowable embolic material as the flowable embolic material flows between the first chamber and the second chamber.

2. The system of claim 1, wherein:
a) with the second actuator opening the first flow path, actuation of the first actuator causes the flowable embolic material to exit the first chamber, pass along the first flow path through the mixing component to mix the flowable embolic material and into the second chamber, thereby directing the second piston to the retracted position of the second piston, and, upon release of the first actuator, the second piston automatically returns back towards the discharge position of the second piston to cause the flowable embolic material to exit the second chamber, pass along through the first flow path through the mixing component to further mix the flowable embolic material and into the first chamber; and
b) with the second actuator thereafter opening the second flow path, actuation of the first actuator causes the flowable embolic material to exit the first chamber, pass along through the second flow path and out the outlet.

3. The system of claim 1, further comprising a tubular member coupled to the outlet of the diverter, the tubular member comprising a proximal end, a distal end sized for introduction into the body of the patient, and a lumen extending between the proximal end of the tubular member and the distal end of the tubular member for delivering the flowable embolic material from the outlet out the distal end of the tubular member.

4. The system of claim 3, wherein the proximal end of the tubular member and the outlet of the diverter comprise one or more connectors for removably connecting the proximal end of the tubular member and the outlet.

5. The system of claim 3, wherein the tubular member comprises a catheter, the system further comprising a length of flexible tubing extending between the outlet and the proximal end of the catheter.

6. The system of claim 3, further comprising a filter coupled to the proximal end of the tubular member and the outlet.

7. The system of claim 6, wherein the filter comprises an air-bleed filter for removing gas from the flowable embolic material before introducing the flowable embolic material into the lumen of the tubular member.

8. The system of claim 1, further comprising a tubular member connectable to the outlet of the diverter, the tubular member comprising a proximal end, a distal end sized for introduction into the body of the patient, and a lumen extending between the proximal end of the tubular member and the distal end of the tubular member for delivering the flowable embolic material from the outlet out the distal end of the tubular member.

9. The system of claim 1, wherein the diverter comprises a two-way manifold in the housing.

10. The system of claim 1, wherein the second piston is biased to the discharge position of the second piston by a mechanism within the housing that stores energy when activated.

11. The system of claim 1, wherein the second piston is biased to the discharge position of the second piston by a spring within the housing.

12. The system of claim 1, wherein the static mixing elements are arranged sequentially such that the flowable embolic material passing through the mixing component is mixed by the static mixing elements.

13. The system of claim 12, wherein the static mixing elements comprise one or more helical elements or flow dividers.

14. The system of claim 1, wherein the first chamber is located within a barrel of a syringe, and wherein the first actuator comprises a plunger extending from the barrel of the syringe and coupled to the first piston such that manual advancement of the plunger causes the first piston to move from the retracted position of the first piston to the discharge position of the first piston.

15. The system of claim 1, wherein the diverter comprises a manifold including a first manifold port communicating with the first port of the first chamber, a second manifold port communicating with the second port of the second chamber, and a third manifold port communicating with the outlet, and wherein the mixing component is located along the first flow path between the second manifold port and the second port of the second chamber.

16. The system of claim 1, wherein the mixing component further comprises internal features sized to interfere with the static mixing elements and prevent proximal or distal translation of the static mixing elements with respect to the elongate member.

17. The system of claim 1, wherein the static mixing elements comprise a plurality of helical static mixers housed within the elongate member.

18. The system of claim 1, wherein the first chamber is located within a source syringe that is external to the housing.

19. The system of claim 18, wherein the system comprises a mixing syringe mounted in the housing that includes the second chamber of the barrel.

20. The system of claim 19, wherein the second chamber is the only chamber within the mixing syringe.

21. The system of claim 1, wherein the housing includes one or more mounting features for limiting movement of the barrel and the mixing component within the housing.

22. The system of claim 1, wherein the second piston is biased to the discharge position of the second piston by a spring mounted within a chamber of the housing.

23. The system of claim 1, wherein the second piston is biased to the discharge position of the second piston by a spring mounted within the housing outside the barrel.

\* \* \* \* \*